(12) United States Patent
Huang

(10) Patent No.: US 9,676,008 B1
(45) Date of Patent: Jun. 13, 2017

(54) MULTIFUNCTIONAL JEWELRY CLEANER

(71) Applicant: Anvid Products, Inc., Livermore, CA (US)

(72) Inventor: Weiyuan Huang, Pleasanton, CA (US)

(73) Assignee: Anvid Products, Inc., Livermore, CA (US)

( * ) Notice: Subject to any disclaimer, the term of this patent is extended or adjusted under 35 U.S.C. 154(b) by 0 days.

(21) Appl. No.: 15/180,670

(22) Filed: Jun. 13, 2016

(30) Foreign Application Priority Data

Apr. 13, 2016 (CN) .................... 2016 2 0312895 U

(51) Int. Cl.
*B08B 3/12* (2006.01)
*B08B 3/00* (2006.01)
*B08B 7/00* (2006.01)

(52) U.S. Cl.
CPC .............. *B08B 3/12* (2013.01); *B08B 3/00* (2013.01); *B08B 7/0057* (2013.01)

(58) Field of Classification Search
CPC ....................................................... B08B 3/12
See application file for complete search history.

(56) References Cited

U.S. PATENT DOCUMENTS

| | | | |
|---|---|---|---|
| 2004/0178061 A1* | 9/2004 | Accattato | ................. B08B 3/00 204/241 |
| 2010/0326484 A1* | 12/2010 | Wu | ........................ A61L 2/025 134/56 R |

* cited by examiner

*Primary Examiner* — Jason Ko
(74) *Attorney, Agent, or Firm* — Sheppard Mullin Richter & Hampton LLP

(57) ABSTRACT

A multiple jewelry cleaner having a heat insulation gasket; a front end of an upper surface of the heat insulation gasket is removably configured with a cup; a top part of the cup is removably mounted with a filter net; a front mounting panel is installed on the upper surface of the heat insulation gasket at one side of the cup; an end of the front mounting panel distant from the cup is fixedly installed with a front shell; a nozzle is fixedly installed on and passes through the front mounting panel and the front shell, with a nozzle head positioned external to the front mounting panel and the front shell; two sides of the front shell are fixedly installed with a right cover and a left cover respectively; bottom ends of both the right cover and the left cover rest on the upper surface of the heat insulation gasket.

4 Claims, 1 Drawing Sheet

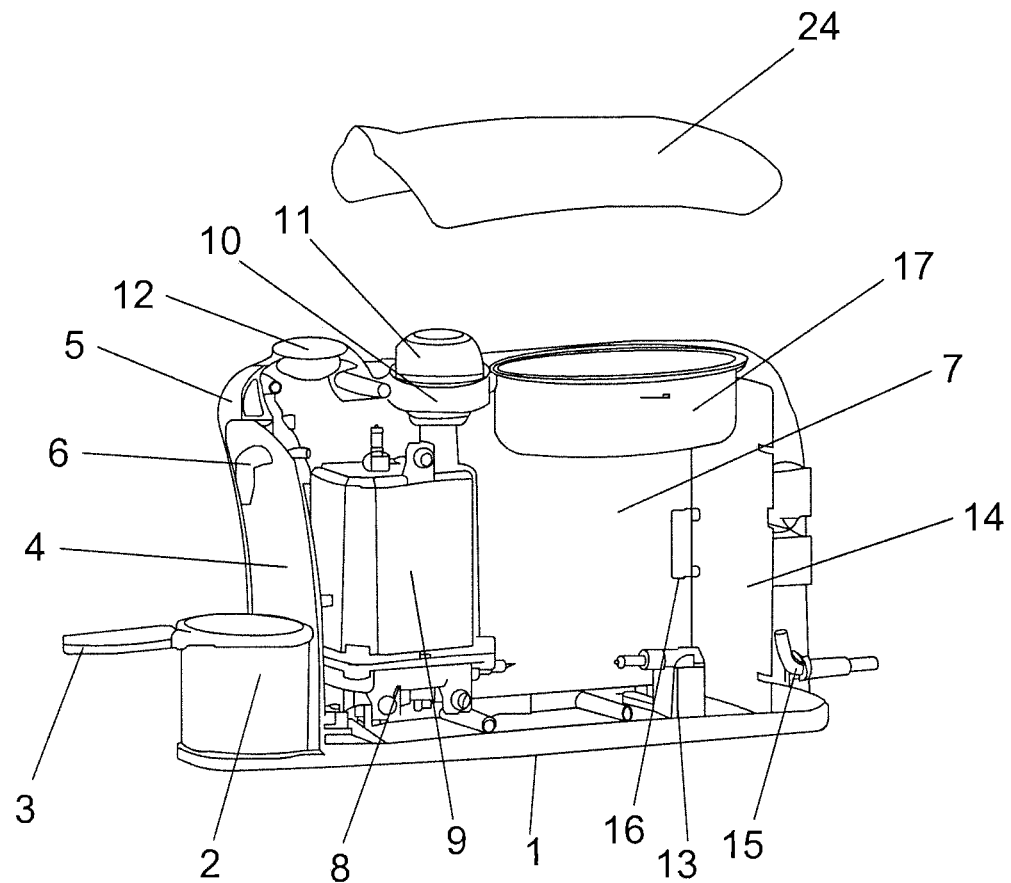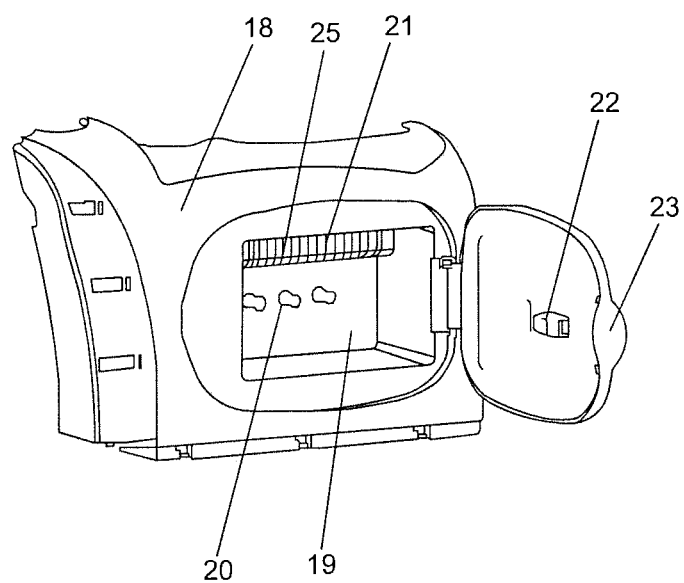

MULTIFUNCTIONAL JEWELRY CLEANER

BACKGROUND

The present disclosure relates to the technological field of ultrasonic steam cleaners, and more specifically relates to a multifunctional jewelry cleaner.

Ultraviolet sterilization damages the molecular structures of DNA or RNA of germs and bacteria by using UV rays emitted from a UV light, thereby causing the death of growth cells and regenerative cells and thus achieving the effect of sterilization and disinfection.

Ultrasonic steam cleaners are often used nowadays for cleaning jewelry. However, the ultrasonic steam cleaners now available in the market are mono-functional. They can only clean limited kinds of objects and most of them can only clean objects made of the same materials. They are therefore very limited in applications, and furthermore, most of them cannot achieve sterilization, and therefore disadvantageous in cleaning special kinds of jewelry. The present disclosure discloses a multifunctional jewelry cleaner to solve the above problems.

SUMMARY

It is an object of the present disclosure to provide a multifunctional jewelry cleaner to solve the problems mentioned in the background section.

The present disclosure adopts the following technical solution to attain the above object: a multifunctional jewelry cleaner comprising a heat insulation gasket; a front end of an upper surface of the heat insulation gasket is removably configured with a cup; a top part of the cup is removably mounted with a filter net; a front mounting panel is fixedly installed on the upper surface of the heat insulation gasket at one side of the cup; an end of the front mounting panel distant from the cup is fixedly installed with a front shell; a nozzle is fixedly installed on the front mounting panel and the front shell, with two ends of the nozzle passing through both the front mounting panel and the front shell, and a nozzle head of the nozzle extending outwardly and positioned external to the front mounting panel and the front shell; two sides of the front shell are fixedly installed with a right cover and a left cover respectively; bottom ends of both the right cover and the left cover rest on the upper surface of the heat insulation gasket.

A bottom side of an inner cavity of the right cover is fixedly installed with a heater lower cover located on the upper surface of the heat insulation gasket; a top part of the heater lower cover is fixedly connected with the heater upper cover; a top part of the heater upper cover is fixedly connected with a water opening valve seat through a water container mouth; the water opening valve seat passes through a top part of the right cover; a press button panel is fixedly installed on the right cover at one side of the water opening valve seat; a solenoid valve is fixedly installed on the upper surface of the heat insulation gasket at one side of the heater lower cover distant from the front shell; a side of the solenoid valve distant from the heater lower cover is fixedly installed with a control panel; a side of the control panel distant from the solenoid valve is fixedly connected with a power wire which passes through the right cover and extend outwardly to an external side of the right cover; a side surface of the control panel is fixedly connected with an inner wall of the right cover through a press piece; an ultrasonic wave basin is provided at a top side of the right cover at a position above the press piece.

A side of the left cover distant from the right cover is provided with a sterilization chamber; hanging pins are fixedly provided inside the sterilization chamber; one end of each of the hanging pins is fixedly connected with the left cover; a top inner side of the sterilization chamber is fixedly provided with a UV light shade right above the hanging pins; a UV light is fixedly mounted inside the UV light shade; a side surface of the left cover is hinged with a door inner shell that matches with the sterilization chamber through hinges; a side surface of the door inner shell is fixedly installed with a door front shell; a top cover is removably mounted on top of the left cover and the right cover.

Preferably, the ultrasonic wave basin comprises a stainless steel basin; an ultrasonic wave generator is adhered at a bottom side of the stainless steel basin; an ultrasonic wave basin seal ring is provided at a top part of the ultrasonic wave basin.

Preferably, a temperature sensor is fixedly installed at a bottom part of the heater lower cover; a heater seal ring is provided at a connection part between the heater lower cover and the heater upper cover.

Preferably, the press button panel comprises a trigger plate and a press plate; the trigger plate is positioned on top of the press plate.

Preferably, there are at least three hanging pins; the hanging pins are fixedly mounted on an inner wall of the sterilization chamber by equal intervals.

Compared with existing prior arts, the present disclosure has the following advantages: the multifunctional jewelry cleaner is provided with heating elements inside the heater lower cover and the heater upper cover to heat up water and generate high pressure and high temperature steam; by operating the press button panel, steam is ejected from the nozzle; items placed beneath the nozzle can be clean and sanitized by high temperature. The ultrasonic wave basin provided by the present disclosure is operable also through the press button panel; water and items to be cleaned are put inside the ultrasonic wave basin where ultrasonic waves generated inside the ultrasonic wave basin cause vibration which cleans the items by ultrasonic waves. The sterilization chamber provided by the present disclosure has the UV light inside the chamber; the sterilization chamber is also operable through the press button panel; when items to be sterilized are put inside the chamber, the UV light is lightened up and emits UV rays to perform UV disinfection of the items.

The multifunctional jewelry cleaner is equipped with the function of UV disinfection so as to provide an alternative option for cleaning and sterilization. Therefore, the multifunctional jewelry cleaner provided by the present disclosure is more powerful in terms of its functions, and it can also clean objects made of different materials, thereby broadening its scope of applications. Furthermore, items that are not suitable for high temperature steam washing or ultrasonic wave cleaning can be disinfected by UV. Therefore, the cleaner can clean more different objects made with different materials and has a broadened scope of applications. It also has the advantage of cleaning special jewelry.

BRIEF DESCRIPTION OF THE DRAWINGS

FIG. 1 illustrates an internal structure of the present disclosure. References in the figures: 1—heat insulation gasket; 2—cup; 3—filter net; 4—front mounting panel; 5—front shell; 6—nozzle; 7—right cover; 8—heater lower cover; 9—heater upper cover; 10—water container mouth; 11—water opening valve seat; 12—press button panel;

13—solenoid valve; 14—control panel; 15—power wire; 16—press piece; 17—ultrasonic wave basin; 18—left cover; 19—sterilization chamber; 20—hanging pins; 21—UV light shade; 22—door inner shell; 23—door front shell; 24—top cover; 25—UV light.

DETAILED DESCRIPTION

The technical solution of an embodiment of the present disclosure will be more fully and clearly described below with reference to the figures illustrating the embodiment of the present disclosure. Obviously, the embodiment described below is only one of the embodiments of the present disclosure. It does not cover all the possible ways to implement the present disclosure. All other embodiments obtainable by a person skilled in this field of art based on the embodiment given in the present disclosure without any need of inventive laboring should also fall within the scope of protection of the present disclosure.

With reference to FIG. 1, the present disclosure provides a multifunctional jewelry cleaner comprising a heat insulation gasket 1 which is capable of preventing overheating and burning of objects at the bottom; a front end of an upper surface of the heat insulation gasket 1 is removably configured with a cup 2; a top part of the cup 2 is removably mounted with a filter net 3; a front mounting panel 4 is fixedly installed on the upper surface of the heat insulation gasket 1 at one side of the cup 2; an end of the front mounting panel 4 distant from the cup 2 is fixedly installed with a front shell 5; a nozzle 6 is fixedly installed on the front mounting panel 4 and the front shell 5, with two ends of the nozzle 6 passing through both the front mounting panel 4 and the front shell 5, and a nozzle head of the nozzle 6 extending outwardly and positioned external to the front mounting panel 4 and the front shell 5; two sides of the front shell 5 are fixedly installed with a right cover 7 and a left cover 18 respectively; bottom ends of both the right cover 7 and the left cover 18 rest on the upper surface of the heat insulation gasket 1.

A bottom side of an inner cavity of the right cover 7 is fixedly installed with a heater lower cover 8 located on the upper surface of the heat insulation gasket 1; heating elements are provided inside the heater lower cover 8 and a heater upper cover 9; such a configuration having the heater lower cover 8, the heater upper cover 9 and the heating elements inside can heat up water and generate high pressure and high temperature steam; by operating a press button panel 12, steam is ejected through the nozzle 6; jewelry can be subject to high temperature steam washing and disinfection when placed under the nozzle 6. A temperature sensor is fixedly installed at a bottom part of the heater lower cover 8 for detecting real time temperature changes. A heater seal ring is provided at a connection part between the heater lower cover 8 and the heater upper cover 9; a top part of the heater lower cover 8 is fixedly connected with the heater upper cover 9; a top part of the heater upper cover 9 is fixedly connected with a water opening valve seat 11 through a water container mouth 10; the water opening valve seat 11 passes through a top part of the right cover 7; the press button panel 12 is fixedly installed on the right cover 7 at one side of the water opening valve seat 11; the press button panel 12 comprises a trigger plate and a press plate; the trigger plate is positioned on top of the press plate for the main purpose of controlling. A solenoid valve 13 is fixedly installed on the upper surface of the heat insulation gasket 1 at one side of the heater lower cover 8 distant from the front shell 5; a side of the solenoid valve 13 distant from the heater lower cover 8 is fixedly installed with a control panel 14; a side of the control panel 14 distant from the solenoid valve 13 is fixedly connected with a power wire 15 which passes through the right cover 7 and extend outwardly to an external side of the right cover 7; a side surface of the control panel 14 is fixedly connected with an inner wall of the right cover 7 through a press piece 16; an ultrasonic wave basin 17 is provided at a top side of the right cover 7 at a position above the press piece 16; the ultrasonic wave basin 17 can generate ultrasonic waves so that the multifunctional jewelry cleaner can clean jewelry not only by high temperature steam washing and disinfection, but also by ultrasonic cleaning in the ultrasonic wave basin. When using the ultrasonic wave basin 17, water and jewelry to be cleaned are added into the ultrasonic wave basin 17; the ultrasonic wave basin 17 is operable through the press button panel 12; vibration of ultrasonic waves in the ultrasonic wave basin 17 can clean the jewelry by ultrasonic waves. The ultrasonic wave basin 17 comprises a stainless steel basin; an ultrasonic wave generator is adhered at a bottom side of the stainless steel basin; an ultrasonic wave basin seal ring is provided at a top part of the ultrasonic wave basin 17.

A side of the left cover 18 distant from the right cover is provided with a sterilization chamber 19 which is also operable through the press button panel 12 so that a UV light 25 inside the sterilization chamber 19 is lightened up and emit UV rays to sterilize the jewelry by UV rays; hanging pins 20 are fixedly provided inside the sterilization chamber 19; one end of each of the hanging pins 20 is fixedly connected with the left cover 18; there are at least three hanging pins 20; the hanging pins 20 are fixedly mounted on an inner wall of the sterilization chamber 19 by equal intervals; the hanging pins 20 can hang charms and jewelry etc. A top inner side of the sterilization chamber 19 is fixedly provided with a UV light shade 21 right above the hanging pins 20. The UV light 25 is fixedly mounted inside the UV light shade 21. A side surface of the left cover 18 is hinged with a door inner shell 22 that matches with the sterilization chamber 19 through hinges. A side surface of the door inner shell 22 is fixedly installed with a door front shell 23. A top cover 24 is removably mounted on top of the left cover 18 and the right cover 7. The top cover 24 tightly integrates the entire multifunctional jewelry cleaner. The multifunctional jewelry cleaner is equipped with the function of UV disinfection so as to provide an alternative option for cleaning and sterilization. Therefore, the multifunctional jewelry cleaner provided by the present disclosure is more powerful in terms of its functions, and it can also clean objects made of different materials, thereby broadening its scope of applications. Furthermore, items that are not suitable for high temperature steam washing or ultrasonic wave cleaning can be disinfected by UV. Therefore, the cleaner can clean more different objects made with different materials and has a broadened scope of applications. It also has the advantage of cleaning special jewelry.

During use, open the door inner shell 22 and put the items to be cleaned inside the sterilization chamber 19; close the door inner shell 22 and turn on the UV light 25 to emit UV rays to achieve UV disinfection of the items.

Although the present disclosure has already shown and described an embodiment of the present disclosure, it is known to a person skilled in this field of art that various changes, modification, replacement and variations of the embodiment disclosed herein are possible given that they do not deviate from the principle and essence of the present disclosure. The scope of protection of the present disclosure is defined by the appended claims and their equivalents.

What is claimed is:

1. A multifunctional jewelry cleaner, comprising a heat insulation gasket (1); wherein a front end of an upper surface of the heat insulation gasket (1) is removably configured with a cup (2); a top part of the cup (2) is removably mounted with a filter net (3); a front mounting panel (4) is fixedly installed on the upper surface of the heat insulation gasket (1) at one side of the cup (2); an end of the front mounting panel (4) distant from the cup (2) is fixedly installed with a front shell (5); a nozzle (6) is fixedly installed on the front mounting panel (4) and the front shell (5), with the nozzle (6) passing through both the front mounting panel (4) and the front shell (5), and a nozzle head of the nozzle (6) extending outwardly and positioned external to the front mounting panel (4) and the front shell (5); two sides of the front shell (5) are fixedly installed with a right cover (7) and a left cover (18) respectively; bottom ends of both the right cover (7) and the left cover (18) rest on the upper surface of the heat insulation gasket (1);

a bottom side of an inner cavity of the right cover (7) is fixedly installed with a heater lower cover (8) located on the upper surface of the heat insulation gasket (1); a top part of the heater lower cover (8) is fixedly connected with a heater upper cover (9); a top part of the heater upper cover (9) is fixedly connected with a water opening valve seat (11) through a water container mouth (10); one or more heating elements inside the heater lower cover (8) and the heater upper cover (9); the water opening valve seat (11) passes through a top side of the right cover (7); a press button panel (12) is fixedly installed on the right cover (7) at one side of the water opening valve seat (11); a solenoid valve (13) is fixedly installed on the upper surface of the heat insulation gasket (1) at one side of the heater lower cover (8) distant from the front shell (5); a side of the solenoid valve (13) distant from the heater lower cover (8) is fixedly installed with a control panel (14); a side of the control panel (14) distant from the solenoid valve (13) is fixedly connected with a power wire (15) which passes through the right cover (7) and extend outwardly to an external side of the right cover (7); a side surface of the control panel (14) is fixedly connected with an inner wall of the right cover (7) through a press piece (16); an ultrasonic wave basin (17) is provided at the top side of the right cover (7) at a position above the press piece (16); and a side of the left cover (18) distant from the right cover (7) is provided with a sterilization chamber (19); hanging pins (20) are fixedly provided inside the sterilization chamber (19); one end of each of the hanging pins (20) is fixedly connected with the left cover (18); a top inner side of the sterilization chamber (19) is fixedly provided with a UV light shade (21) right above the hanging pins (20); a UV light (25) is fixedly mounted inside the UV light shade (21); a side surface of the left cover (18) is hinged with a door inner shell (22) that matches with the sterilization chamber (19) through hinges; a side surface of the door inner shell (22) is fixedly installed with a door front shell (23); a top cover (24) is removably mounted on top of the left cover (18) and the right cover (7).

2. The multifunctional jewelry cleaner according to claim 1, wherein the ultrasonic wave basin (17) comprises a stainless steel basin; and an ultrasonic wave basin seal ring is provided at a top part of the ultrasonic wave basin (17).

3. The multifunctional jewelry cleaner according to claim 1, wherein a temperature sensor is fixedly installed at a bottom part of the heater lower cover (8); and a heater seal ring is provided at a connection part between the heater lower cover (8) and the heater upper cover (9).

4. The multifunctional jewelry cleaner according to claim 1, wherein a quantity of the hanging pins (20) is at least three; and the hanging pins (20) are fixedly mounted on an inner wall of the sterilization chamber (19) by equal intervals.

\* \* \* \* \*